US011389187B2

(12) United States Patent
Magno (10) Patent No.: US 11,389,187 B2
(45) Date of Patent: Jul. 19, 2022

(54) RECIPROCATING DRIVE SYSTEM FOR A CUTTING DEVICE

(71) Applicant: GYRUS ACMI, INC., Southborough, MA (US)

(72) Inventor: Joey Magno, Cordova, TN (US)

(73) Assignee: Gyrus ACMI, Inc., Westborough, MA (US)

( * ) Notice: Subject to any disclaimer, the term of this patent is extended or adjusted under 35 U.S.C. 154(b) by 0 days.

(21) Appl. No.: 17/039,199

(22) Filed: Sep. 30, 2020

(65) Prior Publication Data

US 2021/0100575 A1    Apr. 8, 2021

Related U.S. Application Data

(60) Provisional application No. 62/988,051, filed on Mar. 11, 2020, provisional application No. 62/910,541, filed on Oct. 4, 2019.

(51) Int. Cl.
*A61B 17/32* (2006.01)

(52) U.S. Cl.
CPC .................. *A61B 17/32002* (2013.01); *A61B 2017/320028* (2013.01); *A61B 2017/320032* (2013.01)

(58) Field of Classification Search
CPC .. A61B 17/32002; A61B 2017/320028; A61B 2017/320032; A61B 2017/320024; A61B 2017/32004
See application file for complete search history.

(56) References Cited

U.S. PATENT DOCUMENTS

| 4,316,465 A | 2/1982 | Dotson, Jr. |
| 8,006,578 B2* | 8/2011 | Kiester .............. A61B 17/1624 74/23 |
| 10,363,066 B2* | 7/2019 | Magno ................... A61B 17/42 |
| 2019/0021765 A1* | 1/2019 | Magno ............. A61B 17/32002 |

FOREIGN PATENT DOCUMENTS

EP    3403602 A1    11/2018

OTHER PUBLICATIONS

"European Application Serial No. 20199924.0, Extended European Search Report dated Feb. 11, 2021", 10 pgs.

* cited by examiner

*Primary Examiner* — Sarah A Simpson
(74) *Attorney, Agent, or Firm* — Schwegman Lundberg & Woessner, P.A.

(57) ABSTRACT

A reciprocating drive system for a surgical instrument can include a housing defining a central axis. An inner surface of the housing can define a plurality of helical threads extending along the housing. The reciprocating drive system can include a shaft member defining a motive coupler configured to receive torque from a motive source to rotate the shaft member, and a first follower engaged with, and extending radially outward from, the shaft member, and configured to correspondingly engage the plurality of helical threads, such that rotation of the shaft member translates the shaft member laterally along the central axis.

19 Claims, 6 Drawing Sheets

RECIPROCATING DRIVE SYSTEM FOR A CUTTING DEVICE

CROSS-REFERENCE TO RELATED APPLICATION

This application claims the benefit of priority to U.S. Provisional Application No. 62/910,541, filed on Oct. 4, 2019; and U.S. Provisional Application No. 62/988,051, filed on Mar. 11, 2020; the contents of which are incorporated herein in their entireties.

BACKGROUND

The present disclosure relates generally to cutting devices and apparatus used during surgical procedures. For example, arthroscopic, or keyhole procedures, require the use of a surgical cutting instrument that can be inserted into, and cut tissue within, a small incision relative to open procedures. Such cutting instruments utilize a reciprocating drive system to drive a variety of reciprocating or rotating cutting members to cut or resect tissue.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The following description and the drawings sufficiently illustrate specific examples to enable those skilled in the art to practice them. Other examples may incorporate structural, process, or other changes. Portions and features of some examples may be included in, or substituted for, those of other examples. Examples set forth in the claims encompass all available equivalents of those claims.

Surgical cutting instruments suitable for use in open procedures, arthroscopic procedures, ear, nose, and throat (ENT) debridement, or keyhole procedures, can utilize various types of cutting systems to cut or resect tissue. One example of a typical cutting instrument includes a cutting member comprised of a stationary outer tube and a translatable inner tube. Tissue enters an opening in the outer tube and is cut by shear force between the translatable inner tube and the stationary outer tube. Various drive systems exist to drive the cutting member. Generally, such systems include a drive member that is configured to follow a pre-formed drive path to drive the cutting member.

However, existing drive systems typically require numerous components, which can increase the cost of production and reduce the reliability of the drive system. For example, existing systems utilize a drive path formed by a series of threads on a component separate from an external housing. Additionally, in certain situations relatively strong or dense tissue must be cut. The drive system must be robust to apply sufficient force to cut the tissue. Existing drive systems utilize a single drive member to follow the drive path. The force required can cause the single follower to break, or to skip over threads within the drive path, resulting in drive system malfunction or failure.

The present disclosure can address these disadvantages, among others, by providing a reciprocating drive system for a surgical cutting device that can include a housing defining one or more helical threads on an inner surface. The helical threads can form a drive path for one or more followers to follow and correspondingly translate a reciprocating cutting member to cut tissue. The formation of the helical threads on the housing can reduce the number of parts required, by eliminating the need for two separate components to provide the functions of an external housing and a drive path. Reducing the number of parts required can improve the reliability and reduce the cost of production of a reciprocating drive system suitable for arthroscopic use. Additionally, the reciprocating drive system can include two or more followers to increase the force the cutting member can apply and further improve the reliability of the reciprocating drive system.

Figure 1A:
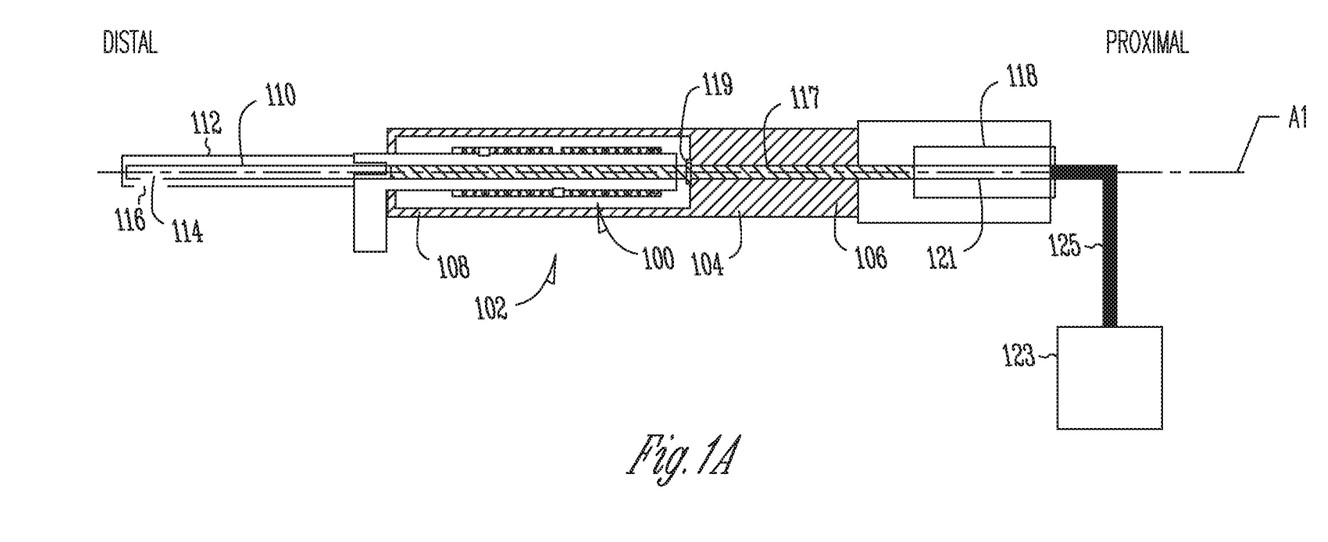
FIG. 1A illustrates a cross-section of a reciprocating drive system positioned within a surgical instrument, in accordance with at least one example of the present application.
Figure 1B:
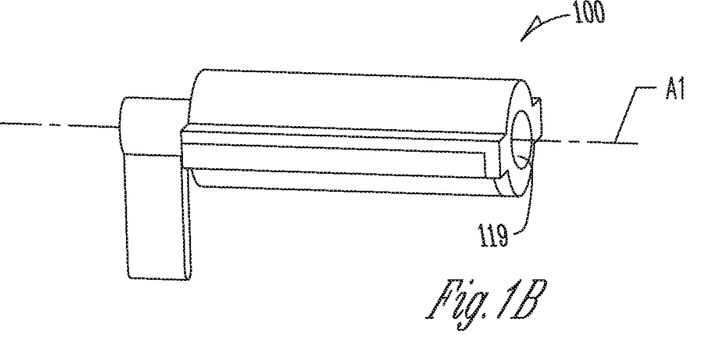
FIG. 1B illustrates a schematic view of a reciprocating drive system, in accordance with at least one example of the present application.

FIG. 1A illustrates a cross-section of the reciprocating drive system 100 positioned within a handle of a surgical instrument 102, in accordance with at least one example of the present application. FIG. 1B illustrates a schematic view of the reciprocating drive system 100, in accordance with at least one example of the present application. Also shown in FIGS. 1A and 1B is a central axis A1, and orientation indicators Proximal and Distal. FIGS. 1A and 1B are discussed below concurrently.

As shown in FIG. 1, the reciprocating drive system 100 can be positioned within a surgical instrument 102. The reciprocating drive system 100 can provide reciprocating drive to the surgical instrument 102. The surgical instrument 102 can be, for example, a motor-assisted arthroscopic cutting device. The surgical instrument 102 can also be a variety of other surgical cutting devices that utilize a reciprocating or a rotating cutting member. The surgical instrument 102 can include an instrument handle 104. The instrument handle 104 can include a proximal portion 106 and a distal portion 108. The proximal portion 106 and the distal portion 108 can be proximal and distal portions, respectively, of the instrument handle 104. The reciprocating drive system 100 can be positioned in various positions within the instrument handle 104, generally between the proximal portion 106 and the distal portion 108.

The surgical instrument 102 can include a cutting member 110 and an outer tube 112. The cutting member 110 can be a cylindrical tube configured to be positionable and translatable within the outer tube 112. The cutting member 110 can be coupled to, and extend distally from, the reciprocating drive system 100. The outer tube 112 can be a cylindrical tube configured to accept the cutting member 110. The cutting member 110 and the outer tube 112 can be fixedly coupled to, and extend distally from the reciprocating drive system 100, or the instrument handle 104. The cutting member 110 can include a cutting window 114. The cutting window 114 can be an opening formed in a generally distal potion of the cutting member 110. The cutting window 114 can have a pair of cutting teeth. The outer tube 112 can include an opening 116. The opening 116 can be an opening formed in a generally distal portion of the outer tube 112. The opening 116 can have a pair of cutting teeth.

In operation, the cutting window 114 can be driven to reciprocate past the opening 116 to cut tissue. In one example, the cutting member 110 and the outer tube 112 can be reusable and fixedly coupled to the instrument handle 104. In another example, the reciprocating drive system 100, the cutting member 110, the outer tube 112, or any combination thereof can be disposable and detachably coupled to the instrument handle 104. The reciprocating drive system 100, the cutting member 110, and the outer tube 112, can also be configured to be used with various existing motorized handles, such as the instrument handle 104. When positioned within the instrument handle 104, the reciprocating drive system 100 can be operable to translate the cutting member 110 proximally and distally along the central axis A1, to cut or resect tissue via reciprocating motion.

The surgical instrument 102 can include a driveshaft 117. The driveshaft 117 can extend within the instrument handle 104 along the central axis A1. The driveshaft 117 can extend within the instrument handle 104 between the proximal portion 106 and the distal portion 108. The driveshaft 117 can be coupled to the reciprocating drive system 100. The driveshaft 117 can extend into the reciprocating drive system 100 through a drive opening 119 formed in a generally proximal end of the reciprocating drive system 100. The driveshaft 117 can also be cannulated, or can otherwise define a bore extending longitudinally through the driveshaft 117 along the central axis A1.

The instrument handle 104 can include a motive source 118. The motive source 118 can be, but is not limited to, an electrically or pneumatically actuated motor. The motive source 118 can include a cannulated shaft 121. The cannulated shaft 121 can extend along the central axis A1, coaxially with the driveshaft 117. The coaxial shaft configuration of the reciprocating drive system 100 and the instrument handle 104 can be simpler and more compact relative to, for example, a drive system including a vertically offset motive source. For example, some devices involving reciprocating and rotary motion utilize a three-shaft system with an offset motor in order to provide the requisite forms of motion.

A proximal portion of the cannulated shaft 121 can be coupled to the driveshaft 117, and a distal portion of the cannulated shaft 121 can be coupled a suction pump 123, via a suction tube 125. The suction pump 123 can thereby apply suction through the suction tube 125, the cannulated shaft 121, and the driveshaft 117, to facilitate transfer of fluid through the surgical instrument 102, such as to help extract tissues or other surgical debris from the reciprocating drive system 100 or to deliver irrigation fluid. After a surgical procedure, the reciprocating drive system 100, the cutting member 110, and the outer tube 112 can be removed from the instrument handle 104 and discarded. This can improve the ease and quality of sterilization of the surgical instrument 102 between surgical procedures. The reciprocating drive system 100 can thereby help perform one or more operations of a surgical procedure.

Figure 2:
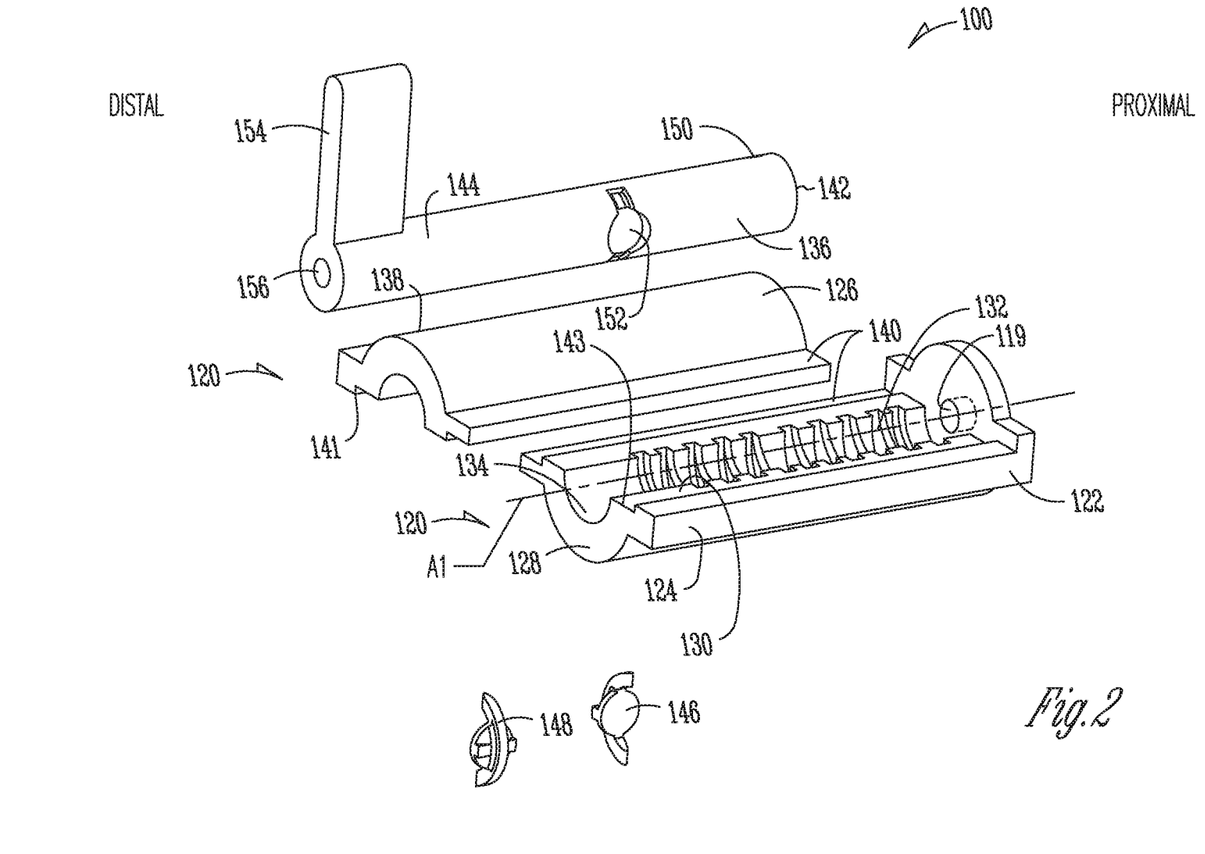
FIG. 2 illustrates an exploded schematic view of a reciprocating drive system, in accordance with at least one example of the present application.

FIG. 2 illustrates an exploded view of the reciprocating drive system 100, in accordance with at least one example of the present application. Also shown in FIG. 2 is a central axis A1, and orientation indicators Proximal and Distal. The reciprocating drive system 100 can include a housing 120 having the drive opening 119, a proximal portion 122, a distal portion 124, a first portion 126, a second portion 128, an inner surface 130, helical threads 132, a non-threaded portion 134, a shaft member 136, an outer surface 138, flanges 140, flange protrusions 141, flange recesses 143, a proximal portion 142, a distal portion 144, a first follower 146, a second follower 148, a first recess 150, a second recess 152, a projection 154, and a bore 156.

The housing 120 can define a central axis A1. The proximal portion 122 and the distal portion 124 can be proximal and distal portions, respectively, of the housing 120. The terms proximal and distal portion as used herein can be relative to an orientation as held by a surgeon during a surgical procedure. The housing 120 can be formed as single piece. The housing 120 can also be formed from multiple pieces. For example, the first portion 126 and the second portion 128 can be separate pieces that can together form the housing 120. The housing 120 can include the inner surface 130. The inner surface 130 can be comprised of an inner surface of both the first portion 126 and the second portion 128. The inner surface 130 can form a generally cylindrical shape.

The inner surface 130 can include and define the helical threads 132. The helical threads 132 can extend along the inner surface 130 of the housing 120, between the proximal portion 122 and the distal portion 124. The inner surface 130 of the housing 120 can also include the non-threaded portion 134. The non-threaded portion 134 can be positioned at the distal portion 124 of the housing 120. The non-threaded portion 134 can be configured to engage the shaft member 136 to position the shaft member 136 along the central axis A1, within the housing 120. The shaft member 136 can extend within the housing 120 between the proximal portion 122 and the distal portion 124. When the shaft member 136 rotates, the non-threaded portion 134 can also function as a bearing surface for the shaft member 136. Although not described in the interest of brevity, second portion 128 can include an inner surface configured as a mirror image of the inner surface 130 such that the helical threads 132 mate with matching helical threads to form one or more double-helical thread paths along the housing 120.

The housing 120 can include the outer surface 138. The outer surface 138 can be comprised of an outer surface of both the first portion 126 and the second portion 128. The outer surface 138 of the housing 120 can form a generally cylindrical shape. The outer surface 138 can also form a generally rectangular, or other three-dimensional shape. The outer surface 138 of the housing 120 can include the flanges 140. The flanges 140 can be protrusions extending radially outward from generally opposite sides of the outer surface 138 of housing 120. The flanges 140 can extend along the outer surface 138 of the housing 120 between the proximal portion 122 and the distal portion 124. The flanges 140 on the first portion 12.6 of the housing 120 can have different dimensions or geometries to the flanges 140 on the second portion 128 of the housing 120.

For example, the flanges 140 of the first portion 126 can include the flange protrusions 141, and the flanges 140 of the second portion 128 can include the flange recesses 143. The flange protrusions 141 can be configured to engage the flange recesses 143, to couple the first portion 126 of the housing 120 to the second portion 128 of the housing 120. The flanges 140 can thereby allow the first portion 126 and the second portion 128 to resists separation due to rotational, lateral, or other operational forces generated during use. Additionally, when the reciprocating drive system 100 is positioned within a surgical instrument, the flanges 140 can help to orient and position the housing 120 within the surgical instrument.

The proximal portion 142 and the distal portion 144 can be proximal and distal portions, respectively, of the shaft member 136. The proximal portion 142 of the shaft member 136 can extend within the proximal portion 122 of the housing 120. The distal portion 144 of the shaft member 136 can extend within the distal portion 124 of the housing 120. The distal portion 144 of the shaft member 136 can also extend distally beyond the distal portion 124 of the housing 120. The shaft member 136 can include the first follower 146. The shaft member 136 can also optionally include the second follower 148. The first follower 146 and the second follower 148 can extend radially outward from the shaft member 136. The first follower 146 and the second follower 148 can be positioned in various orientations along the shaft member 136. The first follower 146 and the second follower 148 can be shaped to correspond to the helical threads 132 formed in the housing 120. The first follower 146 and the second follower 148 can be configured to correspondingly engage and follow the helical threads 132. Optionally, the first follower 146 and the second follower 148 can be interchangeable to reduce the number of different parts needed for manufacture of the reciprocating drive system 100.

The shaft member 136 can include the first recess 150 and the second recess 152. The first recess 150 and the second recess 152 can be formed in the shaft member 136. The first recess 150 and the second recess 152 can be configured to accept and retain the first follower 146 and the second follower 148, respectively. The first recess 150 and the first follower 146 can be sufficiently similar in shape and size to the second recess 152 and the second follower 148, to allow the first follower 146 to be positioned within the second recess 152, and the second follower 148 to be positioned within the first recess 150. When the shaft member 136 is positioned within the housing 120, the first recess 150 and the second recess 152 can be configured to position the first follower 146 and the second follower 148 to engage the helical threads 132. The first recess 150 and the second recess 152 can thereby help to maintain alignment of the shaft member 136 with the central axis A1 when the shaft member 136 rotates.

In some examples, the shaft member 136 can include the projection 154. The projection 154 can extend radially outward from the distal portion 144 of the shaft member 136. The projection 154 can be positioned distally to the distal portion 124 of the housing 120. The projection 154 can extend radially outward beyond an external width, or a height, of the distal portion 124 of the housing 120. The projection 154 can be coupled to or formed on the distal portion 144 of the shaft member 136, in a position sufficiently distal to the housing 120, to allow the projection 154 to rotate and reciprocate proximally and distally along the central axis A1, when the shaft member 136 rotates. The projection 154 can thereby provide convenient access to the distal portion 144 of the shaft member 136 to manually apply rotational, and correspondingly, reciprocating movement to the shaft member 136, when at least the proximal portion 142 of shaft member 136 is disposed within the housing 120.

The shaft member 136 can include the bore 156. The bore 156 can extend within the shaft member 136 between the proximal portion 142 and the distal portion 144. The bore 156 can be configured to accept and engage a driveshaft, such as the driveshaft 117 shown in FIG. 1. The driveshaft 117 can extend through the drive opening 119 formed in the second portion 128 of the housing 120, to engage the bore 156 of the shaft member 136. The bore 156 can function as a motive coupler when engaging a driveshaft coupled to a motive source, such as the driveshaft 117.

The housing 120, the proximal portion 122, the distal portion 124, the first portion 126, the second portion 128, the inner surface 130, the helical threads 132, the non-threaded portion 134, the shaft member 136, the outer surface 138, the flanges 140, the proximal portion 142, the distal portion 144, the first follower 146, the second follower 148, the first recess 150, the second recess 152, the projection 154, and the bore 156 can each be made from, but not limited to, plastic. For example, the components listed above can be made from ABS plastic. The housing 120, the proximal portion 122, the distal portion 124, the first portion 126, the second portion 128, the inner surface 130, the helical threads 132, the non-threaded portion 134, the shaft member 136, the outer surface 138, the flanges 140, the proximal portion 142, the distal portion 144, the first follower 146, the second follower 148, the first recess 150, the second recess 152, the projection 154, and the bore 156 can also be made from stainless steel, or other metals via machining or metallic molding.

As discussed with reference to FIG. 3, when the driveshaft 117 (FIG. 1) and the motive source 118 (FIG. 1) rotate the shaft member 136, the first follower 146 and the second follower 148 can be driven proximally and distally along the helical threads 132 to thereby reciprocate the shaft member 136, while the housing 120 is held in a stationary position within the instrument handle 104 (FIG. 1) by the flanges 140. The single-directional continuous rotation provided by the motive source 118 to the shaft member 136, whether clockwise or counter-clockwise, can result in reciprocation of the shaft member 136.

The shaft member 136 can be configured to slide over the driveshaft 117 to allow for both transmission of rotary input to the shaft member 136, and reciprocation of the shaft member 136. However, the transmission of rotary input to the shaft member 136, and associated reciprocation of the cutting member 110, with or without rotation, can be achieved using a variety of arrangements including couplers, bearings, clutches and the like. For example, the driveshaft 117 can include a male key or male splines configured to mate into a female key or female splines formed in the shaft member 136, to transfer rotary input from the driveshaft 117 to the shaft member 136 while allowing reciprocation along the central axis A1, within a longitudinal length of the key or the splines.

Figure 3:
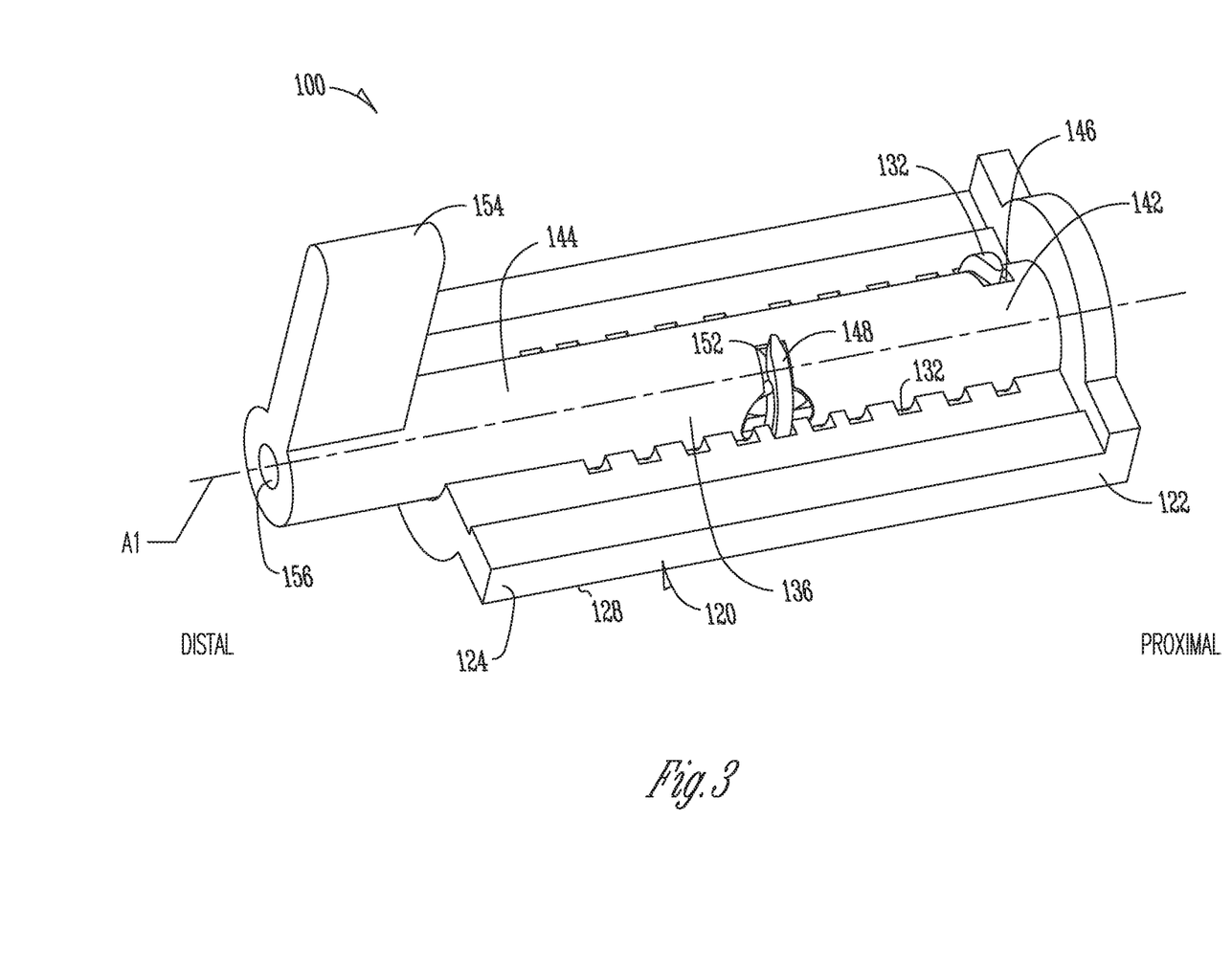
FIG. 3 illustrates a schematic view of a reciprocating drive system, in accordance with at least one example of the present application, with a portion of a housing removed to show a shaft member.

FIG. 3 illustrates a schematic view of the reciprocating drive system 100, in accordance with at least one example of the present application. Also shown in FIG. 3 is a central axis A1, and orientation indicators Proximal and Distal.

The first follower 146 can be positioned within and extend radially outward from the first recess 150 of the shaft member 136. The second follower 148 can engage and extend radially outward from the second recess 152 of the shaft member 136. The first follower 146 and the second follower 148 can be configured to correspondingly engage the helical threads 132. When the shaft member 136 rotates, the first follower 146 and the second follower 148 can follow the helical threads 132 to laterally translate the shaft member 136 along the central axis A1. The shaft member 136 can receive and transfer torque from a motive source to rotate the shaft member 136 within the housing 120. In some examples, the reciprocating cutting system can include the projection 154. The projection 154 can allow a user to manually rotate the shaft member 136 from a position external to the housing 120, to manually reciprocate the shaft member 136 proximally and distally along the central axis A1.

The first follower 146 and the first recess 150 can be laterally spaced apart from the second follower 148 and the second recess 152 along the shaft member 136. For example, the first follower 146 and the first recess 150 can be positioned at the proximal portion 142 of the shall member 136 and the second follower 148 and the second recess 152 can be centrally located on the shaft member 136, generally halfway between the proximal portion 142 and the distal portion 144. The first recess 150 and the second recess 152 can be formed in various other positions on the shaft member 136 generally between the proximal portion 142 and the distal portion 144. The position of the first recess 150 and the second recess 152, and correspondingly, the first follower 146 and the second follower 148, can dictate the distance the shaft member 136 travels laterally within the housing 120. The stroke length of a reciprocating cutting member can thereby be optimized for various surgical procedures based upon the lateral positioning of the first recess 150 and the second recess 152 on the shall member 136.

Additionally, the first recess 150 and the second recess 152 can be formed circumferentially offset positions relative to each other on the shaft member 136. For example, the second recess 152 can be positioned 180 degrees offset relative to the first recess 150. The second recess 152 can also be offset, 45, 90, 135, 225, or 270 degrees offset relative to the first recess 150. The circumferential offset of the first follower 146 relative to the second follower 148 can improve the axial alignment of the shaft member 136 within the non-threaded portion 134 of the housing 120 to prevent binding of the first follower 146 and the second follower 148 within the helical threads 132. The circumferential offset of the first follower 146 relative to the second follower 148 can thereby provide smoother operation of the reciprocating drive system 100, particularly when dense or tough tissues are to be cut.

The helical threads 132 can define a bi-directional helical path for the first follower 146 and the second follower 148 to follow. In operation, when either the first follower 146 or the second follower 148 reaches a proximal or a distal end of the helical threads 132, the first 146 or the second 148 followers can reverse direction and follow the helical threads 132 back in the opposite direction. The helical threads 132 can thereby allow the shaft member 136 to reciprocate through cyclical proximal and distal translation when the shaft member 136 rotates either clockwise or counterclockwise. As discussed with reference to FIG. 4, the helical threads 132 can provide two separate thread paths for the first follower 146 and the second follower 148 to follow, respectively.

Figure 4:
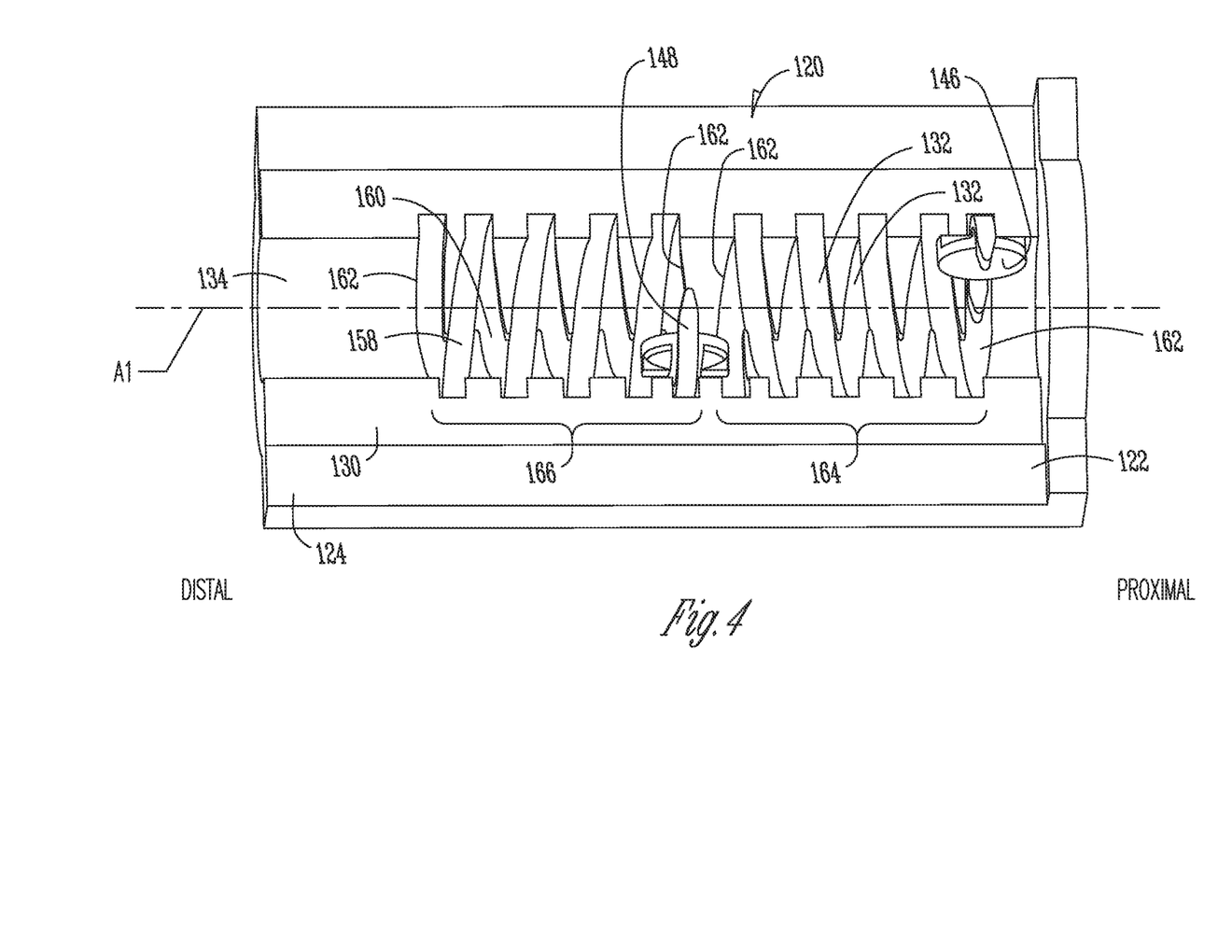
FIG. 4 illustrates a schematic view of a housing, in accordance with at least one example of the present application.

FIG. 4 illustrates a schematic view of the housing 120, in accordance with at least one example of the present application. Also shown in FIG. 4 is a central axis A1, and orientation indicators Proximal and Distal. The reciprocating cutting device 100 can include a first series of threads 158, a second series of threads, and transitional surfaces 162.

As shown in FIG. 4, the helical threads 132 can extend along the inner surface 130 of the housing 120, generally from between the proximal portion 122 and the non-threaded portion 134 at the distal portion 124. A portion of the inner surface 130 of the housing at the proximal portion 122 can also be non-threaded. The helical threads 132 can define a single directional helical path or a bi-directional helical path. The helical threads 132 can include a first thread 158 and a second thread 160.

The first thread 158 can be a first helical thread formed at a first orientation on the inner surface 130 of the housing 120. The second thread 160 can be a second thread formed at a second orientation on the inner surface 130 of the housing 120. The second thread 160 can be formed at different orientation relative to the first thread 158. For example, the first thread 158 can be a right-handed thread and the second thread 160 can be a left-handed thread, or vice versa. As a result, the first thread 158 and the second thread 160 can intersect to together define a bi-directional helical path. For example, the first thread 158 can allow for proximal translation of the shaft member 136 and the second thread 160 can allow for distal translation of the shaft member 136. The helical threads 132 can thereby form a bi-directional helical path for the first follower 146 and the second follower 148 to follow, thereby allowing the shaft member 136 to translate both proximally and distally along the central axis A1.

The helical threads 132 can also define a plurality of transitional surfaces 162. The transitional surfaces 162 can positioned perpendicular to the central axis A1 within the helical threads 132. The transitional surfaces 162 can divide the helical threads 132 into a proximal portion 164 and a distal portion 166. The transitional surfaces 162 can generally define proximal and a distal ends of both the proximal portion 164 and the distal portion 166 of the helical threads 132. The first follower 146 can follow the helical threads 132 within the first portion 164. The second follower 148 can follow the helical threads 132 within the second portion 166.

In operation, the transition surfaces 162 can allow the first follower 146 and the second follower 148 to transition from following the first thread 158 to following the second thread 160, and vice versa. For example, when the first follower 146 and the second follower 148 reach the transitional surfaces 162 at generally proximal or generally distal ends of the first portion 164 and the second portion 166 of the first thread 158, the first follower 146 and the second follower 148 can rotate within first and second recesses 150 and 152, respectively, against the transitional surfaces 162, until the first follower 146 and the second 148 follower each engage the second thread 160. Accordingly, the transitional surfaces 162 can thereby allow the first follower 146 and the second follower 148 to transition from translating proximally within the first thread 158 of the housing 120, to translating distally within the second thread 160 of the housing 120, and vice versa.

Figures 5A, 5B:
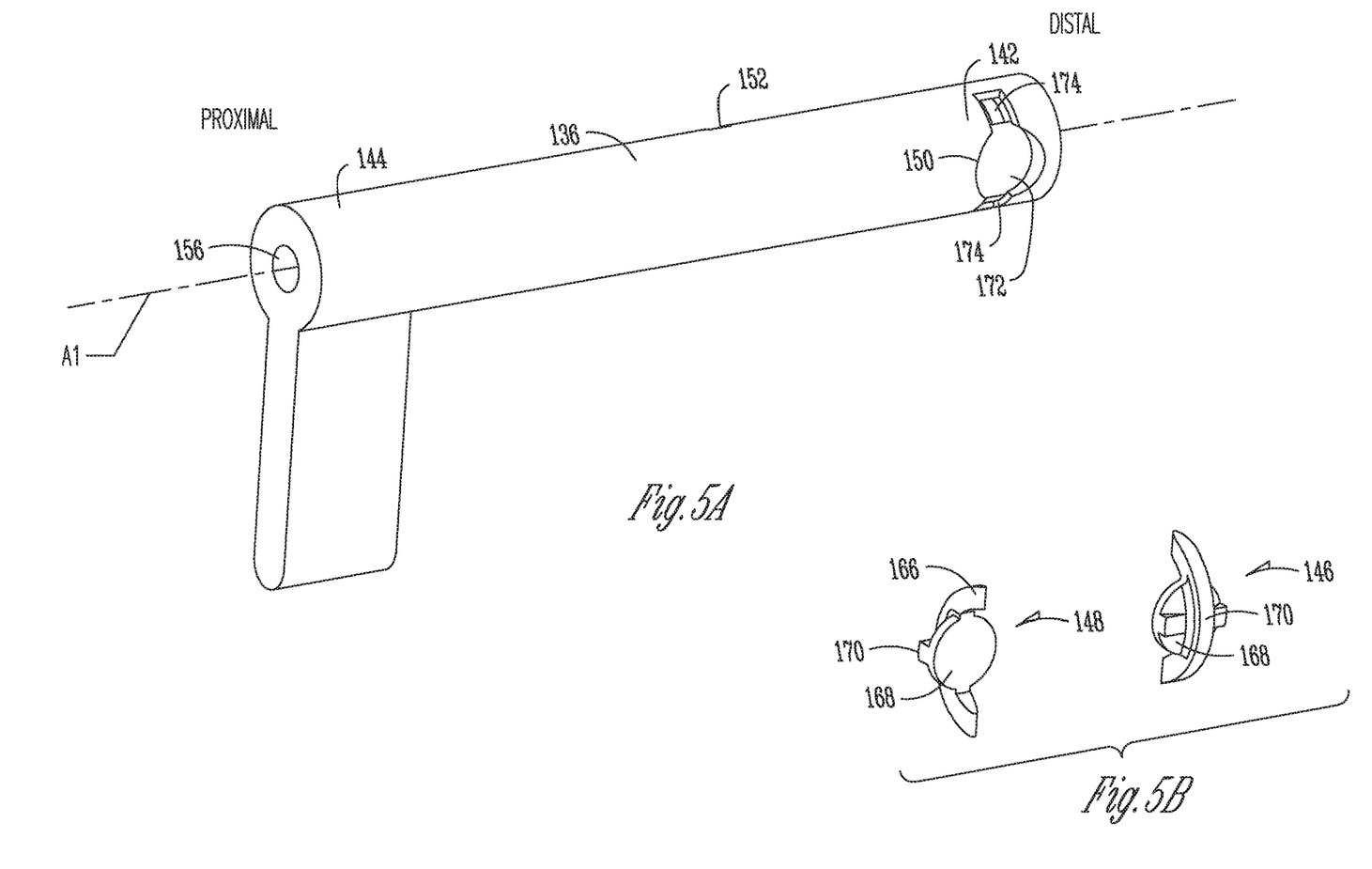
FIG. 5A illustrates a schematic view of a shaft member, in accordance with at least one example of the present application.
FIG. 5B illustrates schematic views of followers, in accordance with at least one example of the present application.

FIG. 5A illustrates a schematic view of a shaft member 136, in accordance with at least one example of the present application. FIG. 5B illustrates schematic views of followers 146 and 148, in accordance with at least one example of the present application. Also shown in FIGS. 5A and 5B is a central axis A1, and orientation indicators Proximal and Distal. FIGS. 5A and 5B are discussed below concurrently.

The first follower 146 and the second follower 148 can each include a body portion 168 and a thread engaging portion 170. The body portion 168 can form a generally circular shape. The body portion 168 can also form a rectangular shape, or a variety of other three-dimensional shapes. The thread engaging portion 170 can extend radially outward from the body portion 168. The thread engaging portion 170 can form a generally semi-circular shape. The thread engaging portion 170 can be configured to correspond to, and engage with, the helical threads 132.

Figure 6:
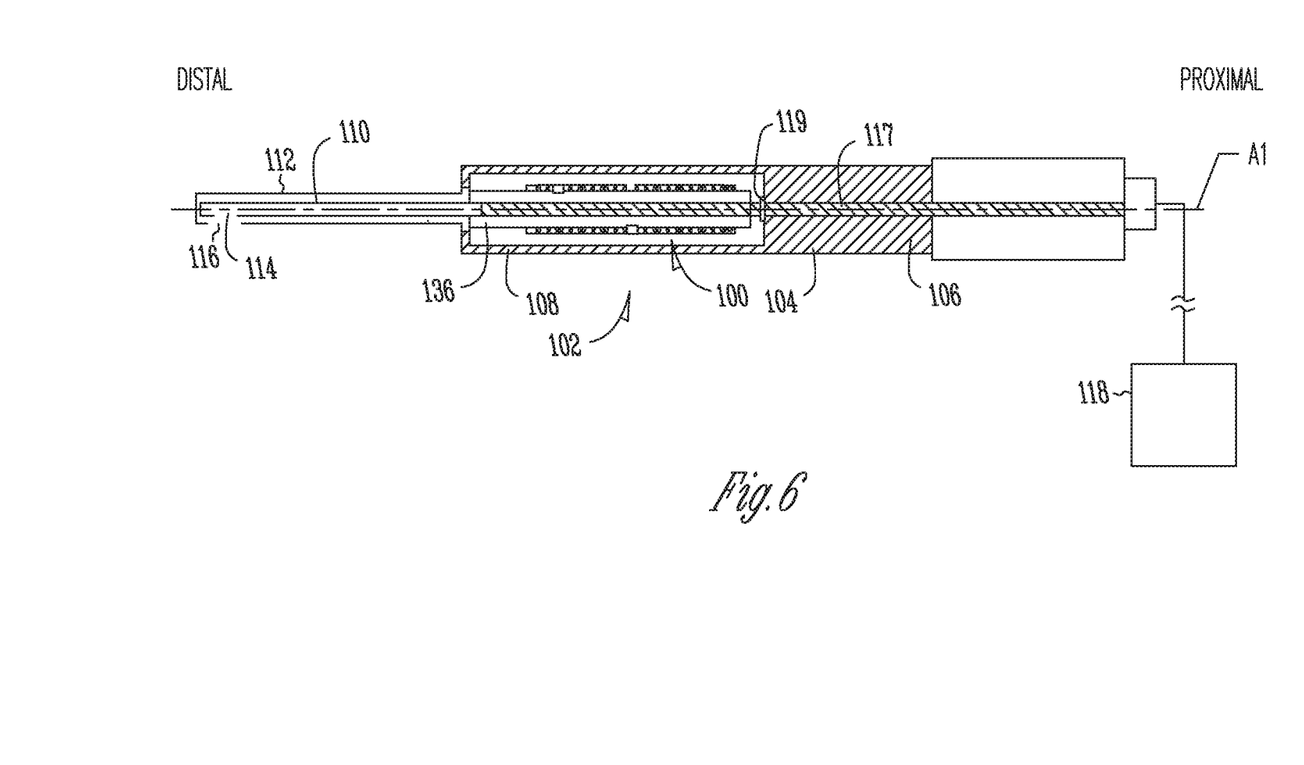
FIG. 6 illustrates a cross-section of a reciprocating drive system positioned within a surgical instrument, in accordance with at least one example of the present application.

The first recess 150 and the second recess 152 can include a central portion 172 and extended portions 174. The central portion 172 can be configured to correspond to and accept the body portion 168 of the first follower 146 and the second follower 148. The central portion 172 can also retain and position first follower 146 and the second follower 148 within first recess 150 and the second recess 152, respectively of the shaft member 136. The extended portions 174 of the first recess 150 and the second recess 152 can be configured to accept ends of the thread engaging portions 170 of the first follower 146 and the second follower 148. The extended portions 174 can be configured to provide sufficient lateral space for the ends of the thread engaging portions 170 to laterally pivot, in order prevent binding between the first follower 146, or the second follower 148, and the helical threads 132, particularly when the shaft member 136 reverses direction, FIG. 6 illustrates a cross-section of a reciprocating drive system positioned within a surgical instrument, in accordance with at least one example of the present application. Also shown in FIG. 6 is a central axis A1, and orientation indicators Proximal and Distal.

As shown in FIG. 6, the projection 154 (FIGS. 2-3) can be omitted from the shaft member 136. The shaft member 136 can be coupled to the cutting member 110. The outer tube 112 can be a stationary cylindrical tube configured to accept the cutting member 110. The outer tube 112 can be coupled to the instrument handle 104. The driveshaft 117 can be coupled to the motive source 118. The driveshaft 117 can extend into the reciprocating drive system 100 through the drive opening 119. The driveshaft 117 can transfer the rotational power to the shaft member 136.

The shaft member 136 can be configured to slide over the driveshaft 117, to allow for both transmission of rotary input to the shaft member 136, and reciprocation of the shaft member 136. The shaft member 136 and the cutting member 110 can rotate and reciprocate within the outer tube 112. When the driveshaft 117 and the motive source 118 rotate the shaft member 136, the single-directional continuous rotation provided by the motive source 118 to the shaft member 136, whether clockwise or counter-clockwise, can result in reciprocation of the shaft member 136. Accordingly, the cutting window 114 of the cutting member 110 can be driven by the shaft member 136, to reciprocate past the opening 116 of the stationary outer tube 112 to cut tissue.

The devices and methods discussed herein provide the benefits of, among others, a simplified reciprocating drive system for use with a motorized surgical cutting instrument. A housing can including an inner surface that defines a plurality of helical threads. One or more followers can engage the plurality of helical threads to drive a cutting member to cut or resect tissue. The simplicity of the reciprocating cutting device can decrease the cost of production, increase the reliability, and make the reciprocating cutting device suitable for disposable use to improve sterilization. Additionally, the inclusion of a second follower can provide improved strength and cutting force over existing reciprocating cutting devices used to drive surgical cutting instruments. The reciprocating drive system is suitable for use in a variety of surgical procedures, including, but not limited to, open procedures, arthroscopic procedures, such as ear, nose, and throat (ENT) debridement, and keyhole procedures.

NOTES AND EXAMPLES

The following, non-limiting examples, detail certain aspects of the present subject matter to solve the challenges and provide the benefits discussed herein, among others.

Example 1 is a reciprocating drive system for a surgical instrument, comprising: a housing defining a central axis, the housing including: a proximal portion and an opposite distal portion; an inner surface and an outer surface, the inner surface defining a plurality of helical threads extending along the proximal portion and the distal portion of the housing; a shaft member positioned along the central axis, the shaft member including a proximal portion and an opposite distal portion, the proximal portion defining a motive coupler configured to receive torque from a motive source to rotate the shaft member; a first follower engaged with, and extending radially outward from, the shaft member and configured to correspondingly engage the plurality of helical threads such that rotation of the shaft member translates the shaft member laterally along the central axis; and a second follower engaged with, and extending radially outward from, the shaft member, the second follower spaced distally along the shaft member from the first follower and configured to correspondingly engage the plurality of helical threads such that rotation of the shaft member translates the shaft member laterally along the central axis.

In Example 2, the subject matter of Example 1 includes, a cutting member coupled to the distal portion of the shaft member and extending distally therefrom, the cutting member operable to cut or resect tissue when the shaft member translates laterally along the central axis.

In Example 3, the subject matter of Examples 1-2 includes, wherein the shaft member includes a first recess and a second recess, the first recess and the second recess configured to receive the first follower and the second follower, respectively, and couple the first follower and the second follower to the shaft member.

In Example 4, the subject matter of Example 3 includes, wherein the first recess is positioned at the proximal portion of the shaft member, and the second recess is positioned at the distal portion of the shaft member.

In Example 5, the subject matter of Examples 1-4 includes, wherein the housing is comprised of a first portion and a second portion, the first portion and the second portion each defining a semi-circular section of the plurality of helical threads on respective inner surfaces, the first portion and the second portion together defining the plurality of helical threads.

In Example 6, the subject matter of Examples 1-5 includes, wherein the plurality of helical threads includes a first helical thread and a second helical thread, the first helical thread defined as right-handed helical threading, and the second helical thread defined as left-handed helical threading.

In Example 7, the subject matter of Example 6 includes, wherein each thread of the first and the second helical threads intersect, such that the first follower and the second follower can transition from following the first helical thread to following the second helical thread when the first follower or the second follower reaches a proximal end, or a distal end, of the first helical thread or the second helical thread, respectively.

In Example 8, the subject matter of Examples 1-7 includes, wherein the distal portion of the shaft member includes a radial projection, the radial projection extending radially outward from the shaft member and positioned distally to the distal portion of the housing, the radial projection operable to rotate the first follower and the second follower from outside of the housing.

Example 9 is a surgical instrument, comprising: An instrument handle having a proximal portion and a distal portion; a housing positioned within the instrument handle and defining a central axis, the housing including: a proximal portion and an opposite distal portion; an inner surface and an outer surface, the inner surface defining a plurality of helical threads extending along the proximal portion and the distal portion of the housing; a shaft member positioned along the central axis, the shaft member including a proximal portion, an opposite distal portion, and a first recess and a second recess, the proximal portion defining a motive coupler configured to receive torque from a motive source to rotate the shaft member; a first follower engaged with and extending radially outward from the first recess of the shaft member, the first follower configured to correspondingly engage the plurality of helical threads such that rotation of the shaft member translates the shaft member laterally along the central axis; and a cutting member coupled to and extending distally beyond the distal portion of the instrument handle from the distal portion of the shaft member, the cutting member operable to cut or resect tissue when the shaft member translates along the central axis.

In Example 10, the subject matter of Example 9 includes, a second follower engaged with and extending radially outward from the second recess of the shaft member, the second follower spaced distally along the shaft member from the first follower and configured to correspondingly engage the plurality of helical threads such that rotation of the shaft member translates the shaft member laterally along the central axis.

In Example 11, the subject matter of Example 10 includes, wherein the first follower and the second follower are engaged with the shaft member in circumferentially offset positions relative to each other.

In Example 12, the subject matter of Example 11 includes, degrees relative to each other.

In Example 13, the subject matter of Examples 10-12 includes, wherein the first follower and the second follower each include a body portion and a thread engaging portion, the thread engaging portion extending radially outward from the body portion and configured to correspondingly engage the plurality of helical threads.

In Example 14, the subject matter of Example 13 includes, wherein the body portion is circular in shape.

In Example 15, the subject matter of Examples 13-14 includes, wherein the body portion is rectangular in shape.

In Example 16, the subject matter of Examples 9-15 includes, wherein the housing is comprised of a first portion and a second portion, the first portion and the second portion each defining a semi-circular section of the plurality of helical threads on respective inner surfaces, the first portion and the second portion together defining the plurality of helical threads.

In Example 17, the subject matter of Examples 9-16 includes, wherein the plurality of helical threads includes a first helical thread and a second helical thread, the first helical thread defined as right-handed helical threading, and the second helical thread defined as left-handed helical threading.

In Example 18, the subject matter of Example 17 includes, wherein each thread of the first and the second helical threads intersect, such that the first follower and the second follower can transition from following the first helical thread to following the second helical thread when the first follower or the second follower reaches a proximal end, or a distal end, of the first helical thread or the second helical thread, respectively.

In Example 19, the subject matter of Examples 9-18 includes, wherein the distal portion of the shaft member includes a radial projection, the radial projection extending radially outward from the shaft member and positioned distally to the distal portion of the housing, the radial projection operable to rotate the first follower and the second follower from outside of the housing.

Example 20 is at least one machine-readable medium including instructions that, when executed by processing circuitry, cause the processing circuitry to perform operations to implement of any of Examples 1-19.

Example 21 is an apparatus comprising means to implement of any of Examples 1-19.

Example 22 is a system to implement of any of Examples 1-19.

Example 23 is a method to implement of any of Examples 1-19.

What is claimed is:

1. A reciprocating drive system for a surgical instrument, comprising:
   a cannulated drive shaft;
   a housing defining a central axis, the housing including:
      a proximal portion and an opposite distal portion, wherein the cannulated drive shaft is configured to extend through the proximal portion of the housing; and
      an inner surface and an outer surface, the inner surface defining a plurality of helical threads extending along the proximal portion and the distal portion of the housing;
   a shaft member positioned along the central axis, the shaft member including a proximal portion and an opposite distal portion, the proximal portion of the shaft member defining a motive coupler configured to receive torque from a motive source via the cannulated drive shaft to rotate the shaft member;
   a first follower engaged with, and extending radially outward from, the shaft member and configured to correspondingly engage the plurality of helical threads such that rotation of the shaft member translates the shaft member laterally along the central axis; and
   a second follower engaged with, and extending radially outward from, the shaft member, the second follower spaced distally along the shaft member from the first follower and configured to correspondingly engage the plurality of helical threads such that rotation of the shaft member translates the shaft member laterally along the central axis.

2. The reciprocating drive system of claim 1, further comprising a cutting member coupled to the distal portion of the shaft member and extending distally therefrom, the cutting member operable to cut or resect tissue when the shaft member translates laterally along the central axis, wherein the cutting member, the shaft member, and the cannulated drive shaft are axially aligned.

3. The reciprocating drive system of claim 1, wherein the shaft member includes a first recess and a second recess, the first recess and the second recess configured to receive the first follower and the second follower, respectively, and couple the first follower and the second follower to the shaft member, wherein the first recess is positioned at the proximal portion of the shaft member, and the second recess is positioned at the distal portion of the shaft member, or at a place between the proximal portion and the distal portion of the shaft member.

4. The reciprocating drive system of claim 1, wherein the housing is comprised of a first portion and a second portion, the first portion and the second portion of the housing each defining a semi-circular section of the plurality of helical threads on respective inner surfaces, the first portion and the second portion of the housing together defining the plurality of helical threads.

5. The reciprocating drive system of claim 1, wherein the plurality of helical threads includes a first helical thread and a second helical thread, the first helical thread defined as right-handed helical threading, and the second helical thread defined as left-handed helical threading.

6. The reciprocating drive system of claim 5, wherein each thread of the first and the second helical threads intersect, such that the first follower and the second follower can transition from following the first helical thread to following the second helical thread when the first follower or the second follower reaches a proximal end, or a distal end, of the first helical thread or the second helical thread, respectively.

7. The reciprocating drive system of claim 1, wherein the distal portion of the shaft member includes a radial projection, the radial projection extending radially outward from the shaft member and positioned distally to the distal portion of the housing, the radial projection operable to rotate the first follower and the second follower from outside of the housing.

8. A surgical instrument, comprising:
an instrument handle having a proximal portion and a distal portion extending along a handle shaft;
a cannulated drive shaft;
a motive source connected to the proximal portion of the instrument handle, the motive source configured to generate rotation of the cannulated drive shaft about a drive axis that is coaxial with the handle shaft;
a housing positioned within the instrument handle and defining a central axis coaxial with the handle shaft, the housing including:
a proximal portion and an opposite distal portion; and
an inner surface and an outer surface, the inner surface defining a plurality of helical threads extending along the proximal portion and the distal portion of the housing;
a shaft member positioned along the central axis, the shaft member including a proximal portion, an opposite distal portion, and a first recess and a second recess, the proximal portion of the shaft member defining a motive coupler connected to the cannulated drive shaft of the motive source to rotate the shaft member coaxially with the drive axis;
a first follower engaged with and extending radially outward from the first recess of the shaft member, the first follower configured to correspondingly engage the plurality of helical threads such that rotation of the shaft member translates the shaft member laterally along the central axis; and
a cutting member coupled to and extending distally beyond the distal portion of the instrument handle from the distal portion of the shaft member, the cutting member operable to cut or resect tissue when the shaft member translates along the central axis.

9. The surgical instrument of claim 8, further comprising a second follower engaged with and extending radially outward from the second recess of the shaft member, the second follower spaced distally along the shaft member from the first follower and configured to correspondingly engage the plurality of helical threads such that rotation of the shaft member translates the shaft member laterally along the central axis.

10. The surgical instrument of claim 9, wherein the first follower and the second follower are engaged with the shaft member in circumferentially offset positions relative to each other.

11. The surgical instrument of claim 9, wherein the first follower and the second follower each include a body portion and a thread engaging portion, the thread engaging portion extending radially outward from the body portion and configured to correspondingly engage the plurality of helical threads.

12. The surgical instrument of claim 11, wherein the body portion is circular in shape.

13. The surgical instrument of claim 11, wherein the body portion is rectangular in shape.

14. The surgical instrument of claim 9, wherein the plurality of helical threads includes a first helical thread and a second helical thread, the first helical thread defined as right-handed helical threading, and the second helical thread defined as left-handed helical threading.

15. The surgical instrument of claim 14, wherein each thread of the first and the second helical threads intersect, such that the first follower and the second follower can transition from following the first helical thread to following the second helical thread when the first follower or the second follower reaches a proximal end, or a distal end, of the first helical thread or the second helical thread, respectively.

16. The surgical instrument of claim 9, wherein the distal portion of the shaft member includes a radial projection, the radial projection extending radially outward from the shaft member and positioned distally to the distal portion of the housing, the radial projection operable to rotate the first follower and the second follower from outside of the housing.

17. The surgical instrument of claim 8, wherein the housing is comprised of a first portion and a second portion, the first portion and the second portion of the housing each defining a semi-circular section of the plurality of helical threads on respective inner surfaces, the first portion and the second portion of the housing together defining the plurality of helical threads.

18. The surgical instrument of claim 8, further comprising:
a tube connected to the cannulated drive shaft;
wherein the cutting member is cannulated such that a fluid path is formed between the cutting member, the cannulated drive shaft and the tube.

19. A reciprocating drive system for a surgical instrument, comprising:
a housing defining a central axis, the housing including:
a proximal portion and an opposite distal portion; and
an inner surface and an outer surface, the inner surface defining a plurality of helical threads extending along the proximal portion and the distal portion of the housing;
a shaft member positioned along the central axis, the shaft member including a proximal portion and an opposite distal portion, the proximal portion or the distal portion of the shaft member defining a motive coupler configured to receive torque from a motive source to rotate the shaft member;

a first follower engaged with, and extending radially outward from, the shaft member and configured to correspondingly engage the plurality of helical threads such that rotation of the shaft member translates the shaft member laterally along the central axis; and a second follower engaged with, and extending radially outward from, the shaft member, the second follower spaced distally along the shaft member from the first follower and configured to correspondingly engage the plurality of helical threads such that rotation of the shaft member translates the shaft member laterally along the central axis;

wherein the distal portion of the shaft member includes a radial projection, the radial projection extending radially outward from the shaft member and positioned distally to the distal portion of the housing, the radial projection operable to rotate the first follower and the second follower from outside of the housing.

* * * * *